(12) United States Patent   (10) Patent No.: US 7,114,645 B2
Felice et al.   (45) Date of Patent: *Oct. 3, 2006

(54) MAIL RECEPTACLE FOR ISOLATING RECEIVED ITEMS IN PUBLIC DROP BOXES

(75) Inventors: Robert J. Felice, Endicott, NY (US); Patrick J. Fitzgibbons, Owego, NY (US); Eugene C. Stradley, Owego, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 239 days.

This patent is subject to a terminal disclaimer.

(21) Appl. No.: 10/315,329

(22) Filed: Dec. 10, 2002

(65) Prior Publication Data

US 2003/0168505 A1   Sep. 11, 2003

Related U.S. Application Data

(60) Provisional application No. 60/339,899, filed on Dec. 10, 2001.

(51) Int. Cl.
*A47G 29/12* (2006.01)
(52) U.S. Cl. .............................. 232/31; 232/30; 232/45
(58) Field of Classification Search ............ 232/30–32, 232/17, 45, 29, 33; 220/23.87
See application file for complete search history.

(56) References Cited

U.S. PATENT DOCUMENTS

| 329,688 A | 11/1885 | Taylor |
| 402,855 A | 5/1889 | Paulsen |
| 435,306 A * | 8/1890 | Hill .............................. 232/24 |
| 726,821 A | 4/1903 | Lambert |
| 948,815 A | 2/1910 | Ehrlich |
| 1,256,044 A | 2/1918 | Schilling |
| 1,338,400 A | 4/1920 | Sachs |
| 1,451,343 A * | 4/1923 | Panagopolous ............... 232/30 |

(Continued)

FOREIGN PATENT DOCUMENTS

DE   136666   12/1902

(Continued)

OTHER PUBLICATIONS

WO 03/050005 A2, Published PCT International Application, Publication Date Jun. 19, 2003, PCT/US02/39113.

(Continued)

*Primary Examiner*—William L. Miller
(74) *Attorney, Agent, or Firm*—Burns & Levinson LLP; Jacob N. Erlich; Harvey Kaye

(57) ABSTRACT

A closeable mail receptacle for use inside of a drop box, includes a rectangular tub having an open top, and a top cover adapted to engage the open top and close the tub either prior to or during removal of the tub from the drop box. The top cover may include a peripheral frame adapted to engage the open top. The rectangular tub may be a standard mail flat tub and further include a non-permeable liner located within the common mail flat tub. The rectangular tub may include a peripheral flange extending horizontally outwardly from around the open top.

13 Claims, 8 Drawing Sheets

U.S. PATENT DOCUMENTS

| | | | |
|---|---|---|---|
| 3,322,477 | A | 5/1967 | Armijo |
| 3,982,690 | A | 9/1976 | Krizan et al. |
| 4,363,438 | A | 12/1982 | Connor |
| 4,593,816 | A | 6/1986 | Langenbeck |
| 4,715,498 | A | 12/1987 | Hanifl |
| 5,316,733 | A | 5/1994 | Rune et al. |
| 5,531,346 | A | 7/1996 | Mosior |
| 6,202,849 | B1 | 3/2001 | Graham |
| 6,277,233 | B1 * | 8/2001 | Daley ............... 156/308.2 |
| 6,592,026 | B1 | 7/2003 | Vilardi |
| 6,742,703 | B1 | 6/2004 | Esakov et al. |
| 6,892,934 | B1 * | 5/2005 | Avant ............... 232/30 |
| 2003/0106929 | A1 * | 6/2003 | Day et al. ............... 232/30 |
| 2003/0127505 | A1 | 7/2003 | Avant |
| 2003/0136823 | A1 * | 7/2003 | Felice et al. ............... 232/30 |
| 2003/0222132 | A1 | 12/2003 | Esakov et al. |
| 2003/0226884 | A1 * | 12/2003 | Swider et al. ............... 232/26 |
| 2005/0008533 | A1 * | 1/2005 | Avant ............... 422/28 |

FOREIGN PATENT DOCUMENTS

| | | |
|---|---|---|
| DE | 1956059 | 2/1967 |
| DE | 1982064 | 3/1968 |
| DE | 1759533 | 1/1970 |
| GB | 2310422 A * | 8/1997 |

OTHER PUBLICATIONS

WO 03/047401 A3 with International Search Report, Jul. 23, 2003, PCT/US02/38646.

U.S. Postal Service Emergency Preparedness Plan for Protecting Postal Employees and Postal Customers from Exposure to Biohazardous Material and for Ensuring Mail Security Against Bioterror Attacks; Mar. 6, 2002; published by USPS.

International Search Report, Sep. 1, 2003, PCT/US02/39113.

WO 03/047401, Published PCT International Application, Publication Date Jun. 12, 2003, PCT/US02/38646.

U.S. Appl. No. 60/339,899, filed Dec. 10, 2001. Applicant: Eugene Stradley. Title: Secure Collection Box.

Copending U.S. Appl. No. 10/309,541, filed Dec. 4, 2002. Applicants: John T. Swider et al. Title: Public Drop Box For Isolating Received Items.

Copending U.S. Appl. No. 10/395,920, filed Mar. 24, 2003. Applicants: John T. Swider et al. Title: Drop Box For Isolating Received Items.

* cited by examiner

MAIL RECEPTACLE FOR ISOLATING RECEIVED ITEMS IN PUBLIC DROP BOXES

RELATED APPLICATIONS

The present application claims priority for U.S. Provisional Patent Application Ser. No. 60/339,899, filed Dec. 10, 2001 and entitled SECURE COLLECTION BOX.

FIELD OF THE INVENTION

The present invention generally relates to depository boxes, such as mail boxes, and in particular to closeable containers used within such drop boxes.

BACKGROUND OF THE INVENTION

The recent incidents of anthrax-laced letters being transported through the United States Postal Service (USPS) facilities by unsuspecting mail handlers to unsuspecting recipients has alarmed the nation and the world. Currently, the tainted letters are discovered after the recipient accepts delivery or by alert postal employees noticing white powder that could be anthrax on mail parcels, sorting and distribution equipment, or themselves. There appear to be no current security devices or procedures that are available to intercept such letters at the earliest source of introduction into the USPS system.

Therefore, it would be advantageous to be able to isolate items dropped into mail boxes and other public drop boxes, so that adequate testing may be performed to detect the presence of any contaminants.

SUMMARY OF THE INVENTION

Accordingly, the present invention provides a closeable mail receptacle for use inside of a drop box, including a rectangular tub having an open top, and a top cover adapted to engage the open top and close the tub either prior to or during removal of the tub from the drop box.

The rectangular tub may include a peripheral edge surrounding said open top and the top cover may include a peripheral frame adapted to engage the peripheral edge. The top cover may include an opening for receiving mail articles and a door adapted for closing the opening prior to removal of the receptacle from the drop box. The door may be hinged to the peripheral frame. The top cover may be adapted to engage the rectangular tub to maintain engagement between the peripheral frame and the peripheral edge. The top cover may include a separate end extension located at two opposing ends of the top cover and arranged to squeeze opposing sides of the rectangular tub.

The rectangular tub may include a common mail flat tub having a separate hand hole located on opposing ends, and the extensions may be adapted to close the hand holes when the top cover engages the rectangular tub. The end extensions may include hand cups adapted for location within the hand holes in the common mail flat tub and may be adapted to allow manual insertion to facilitate handling of the common mail flat tub with the top cover.

The rectangular tub may alternatively include a separate manual grip located on two opposing ends of the rectangular tub, and the top cover may be adapted to engage the manual grips to maintain engagement between the peripheral frame and the open top.

The original peripheral frame or the door may be a single molded piece of polyethylene terephthalte glycol. Independently, the original door may be hinged to said frame by a living hinge, which may be molded from polyvinyl chloride and affixed to the door and frame.

The original rectangular tub may be molded as a single piece with ABS plastic. Alternatively, the original rectangular tub may be a standard mail flat tub, with the receptacle further including a non-permeable liner located within the common mail flat tub. The liner may include an open top, and the top cover may include a peripheral frame adapted to engage the open top of the rectangular tub and the open top of the liner.

The original rectangular tub may include a peripheral flange extending horizontally outwardly from around the open top, and the top cover may be adapted to engage the flange for closing the tub. This top cover may be adapted to engage the flange and close the tub during removal of the tub from the drop box. The top cover may be rectangular and include a lip on at least two opposing sides, which lip is adapted to engage the flange. The flange may be adapted to engage separate opposing rails within the drop box for substantially supporting the receptacle. The top cover may be adapted to engage the opposing rails and to thereby engage the flange with removal of the receptacle from the drop box. A first tub may be adapted to abut a second tub as the first tub is being inserted into a drop box and thereby push the second tub from the drop box in the process of the first tub being pushed into the drop box. Alternatively, a first tub may be adapted to be coupled to a second tub as the first tub is being removed from a drop box and thereby pull the second tub into the drop box in the process of the first tub being pulled from the drop box.

BRIEF DESCRIPTION OF THE DRAWINGS

The present invention is illustratively shown and described in reference to the accompanying drawings in which.

DETAILED DESCRIPTION OF THE DRAWINGS

Figures 1, 2:
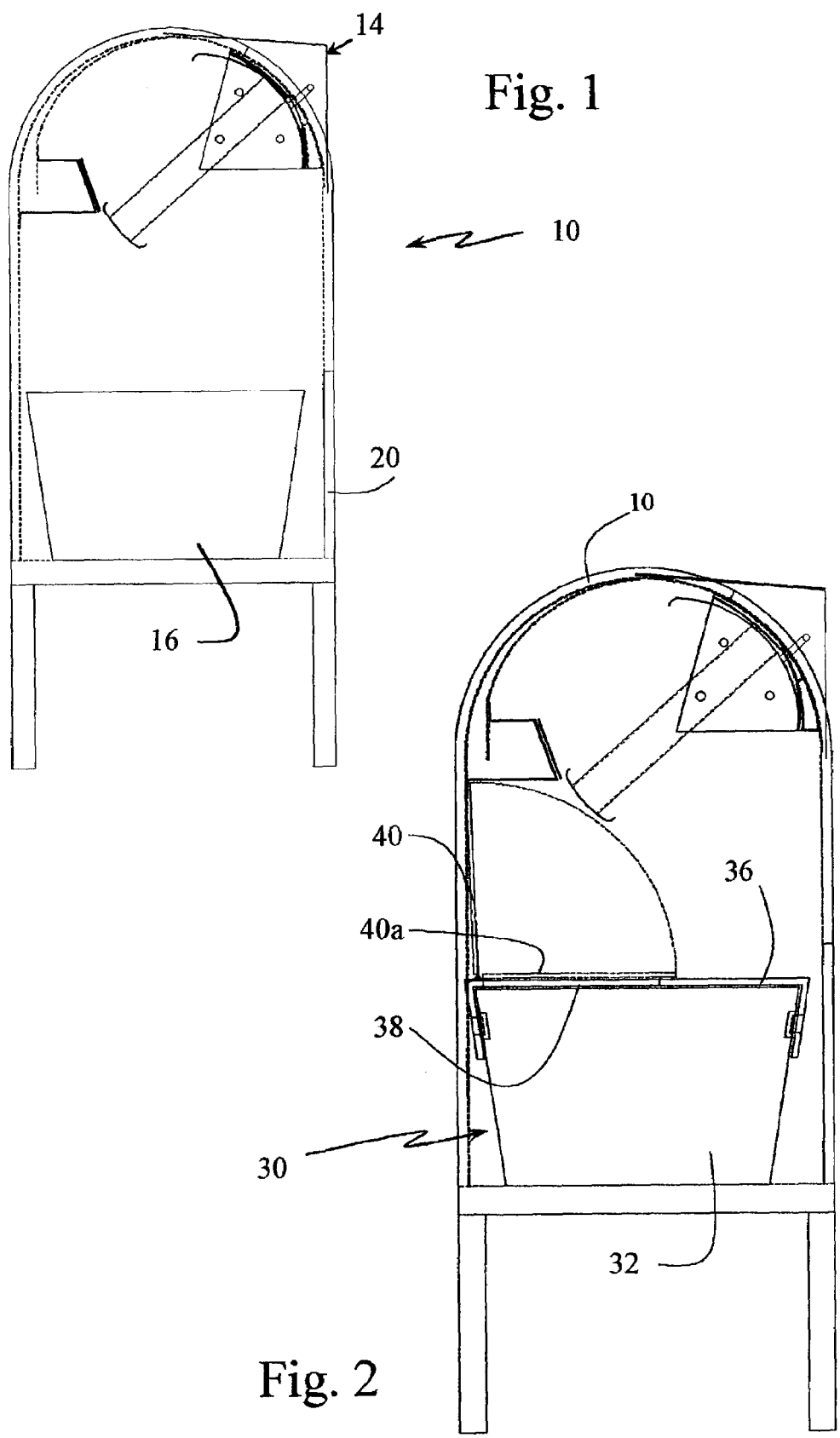
FIG. 1 is a side view diagram of a mail box within which is located a standard mail flats tub.
FIG. 2 is another side view diagram of a mail box within which is located a mail receptacle constructed in accordance with one embodiment of the present invention.

The present invention is best understood in the context of a mail drop box 10 as shown in FIG. 1, which mail box 10 functions to isolate deposited mail items from both the public and from mail carriers. Mail is typically deposited through a depository port 14 and falls into a standard mail flats tub 16. Depository port 14 is shown in an improved version which isolates potential contaminants within mail box 10 and away from members of the public. Depository port 14 is described in greater detail in copending U.S. patent application entitled PULBIC DROP BOX FOR ISOLATING RECEIVED ITEMS, filed Dec. 4, 2002 and owned by the assignee of the present invention.

During scheduled mail pickups, postal carriers typically remove mail flats tub 16 from mail box 10 using a securable door 20. During this removal, mail carriers are potentially exposed to any particulate contaminants maliciously droped into tub 16.

FIG. 2 shows an improved mail receptacle 30 of the present invention located within the mail box 10. Mail receptacle 30 includes a rectangular tub 32, having an open top, and a top cover 36 constructed to close the open top of rectangular tub 32. Top cover 36 is shown to have an opening 38 for receiving mail articles and a door 40 adapted for closing opening 38 prior to removal of mail receptacle 30 from mail box 10. Door 40 is also shown in phantom in its closed position 40a.

Figure 3:
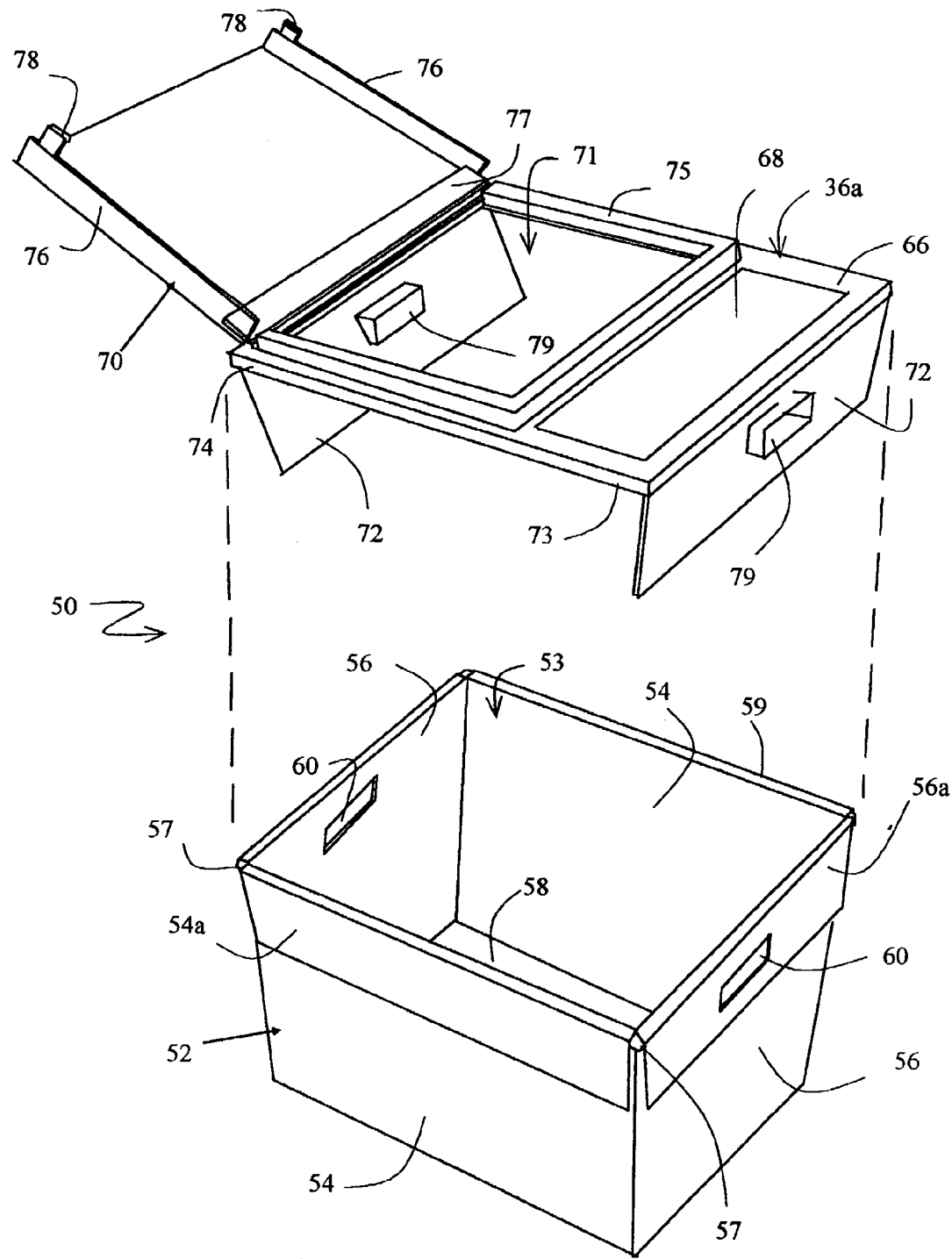
FIG. 3 is an exploded perspective view of a mail receptacle constructed in accordance with another embodiment of the present invention.

FIG. 3 shows an exploded view of a mail receptacle 50 constructed in accordance with one embodiment of the present invention. Mail receptacle 50 generally includes a standard mail flats tub 52 and a top cover 36a. This construction of mail receptacle 50 is designed as a retro fit for the standard mail flats tub 52.

Standard mail flats tub 52 is typically constructed having an open top 53, two opposing sides 54, two opposing ends 56 and a bottom 58. Hand holes 60 are cut through the two opposing ends 56 to allow tub 52 to be easily carried. Tub 52 is typically constructed from corrugated plastic and portions 54a, 56a of respective sides 54 and ends 56 are separated and wrapped around a peripheral wire 57 to provide rigidity to a peripheral top edge 59. The sides 54 and ends 56 are also canted inwardly towards bottom 58 to allow efficient nesting or stacking of multiple tubs 52, whether they include mail articles or not.

Top cover 36a is rectangular and generally includes a peripheral frame 66, a fixed panel 68 and a hinged door 70. Top cover 36a also includes a pair of extensions 72 affixed to opposing ends 73, 74 of top cover 36a, which extensions 72 are constructed to engage tub 52. Extensions 72 are also further constructed to seal hand holes 60. Peripheral frame 66 is designed to substantially seal around peripheral edge 59 of mail flats tub 52 and extensions 72 squeeze opposing ends of tub 52 to maintain that seal. Panel 68 is affixed across one end 73 of frame 66. The combination of frame 66 and panel 68 leaves an opening 71 in top cover 36a for receiving deposited mail articles. Opening 71 (or door 70) may be surrounded, at least on three sides, by a suitable seal 75 to prevent the leakage of air and particulate contaminants from within mail receptacle 50. In one embodiment, seal 75 is formed from compressible neoprene rubber.

Door 70 is hinged to the other end 74 of frame 66 by a hinge 77 and is designed to close opening 71. Door 70 may also include a pair of opposing side flaps 76 to enhance the function and stability of seal 75. A suitable latch 78 may be included to maintain the closure of door 70. In one embodiment, latch 78 is embodied in a pair of opposing hooks are used to engage frame 66 when cover 70 is closed.

As mentioned, extensions 72 are intended to seal hand holes 60 of standard mail flats tub 52. Extensions 72 each further includes a hand cup 79 designed to extend into hand holes 60 which hand cups 79 are adapted for manual insertion to allow mail receptacle 50 to be carried.

Top cover 36a may be constructed from any suitable materials. In one embodiment, frame 66, panel 68, end extensions 72 and hand cups 79 are all formed from a single piece of molded plastic, such as PolyEthylene Terephthalte Glycol Modified (PETG), which is clear. Door 70 may be similarly constructed or alternatively constructed of polycarbonate. Hinge 77 may be any suitable hinge which preferably forms a seal with frame 66 to prevent the escape of contaminants. In one embodiment, a living hinge is used. Living hinges are well known and used in various applications such as tool and tackle boxes and CD containers. As in the present embodiment, hinge 77 may be formed from polyvinyl chloride and then affixed to frame 66 and door 70 by any suitable method, such as a chemical bonding agent like metholene chloride. Suitable alternative constructions may also be used.

Mail receptacle 50 is formed by the location of top cover 36a on the standard mail flats tub 52 as generally depicted for tub 32 and cover 36 of FIG. 2. This assembly significantly reduces the amount of air which passes from a closed receptacle and the particulate contaminants carried by such air.

In this manner, receptacle 50 includes rectangular tub 52 having an open top 53, and a top cover 36a adapted to engage open top 53 and close tub 52 either prior to or during removal of receptacle 50 from a drop box 10 (FIG. 2). Rectangular tub 52 includes a peripheral edge 59 and top cover 36a includes a peripheral frame 66 adapted to engage peripheral edge 59. Top cover 36a includes an opening 71 for receiving mail articles and a door 70 adapted for closing opening 71 prior to removal of receptacle 50 from drop box 10 (FIG. 2). Door 70 may be hinged to peripheral frame 66. Top cover 36a is further adapted to engage rectangular tub 52 to maintain engagement between peripheral frame 66 and peripheral edge 59. Top cover 36a may include a separate end extension 72 located at two opposing ends 73, 74 of top cover 36a and arranged to squeeze opposing ends 56 of rectangular tub 52.

The rectangular tub 52 includes a common mail flat tub having a separate hand hole 60 located on opposing ends, and extensions 72 are adapted to close hand holes 60 when top cover 36a engages rectangular tub 52. End extensions 72 include hand cups 79 adapted for location within hand holes 60 and are adapted to allow manual insertion to facilitate handling of the common mail flat tub with top cover 36a.

The original peripheral frame 66 or door 70 is a single molded piece of polyethylene terephthalte glycol. The original door 70 is hinged to frame 66 by a living hinge 77, which may be molded from polyvinyl chloride and affixed to door 70 and frame 66.

Figure 4:
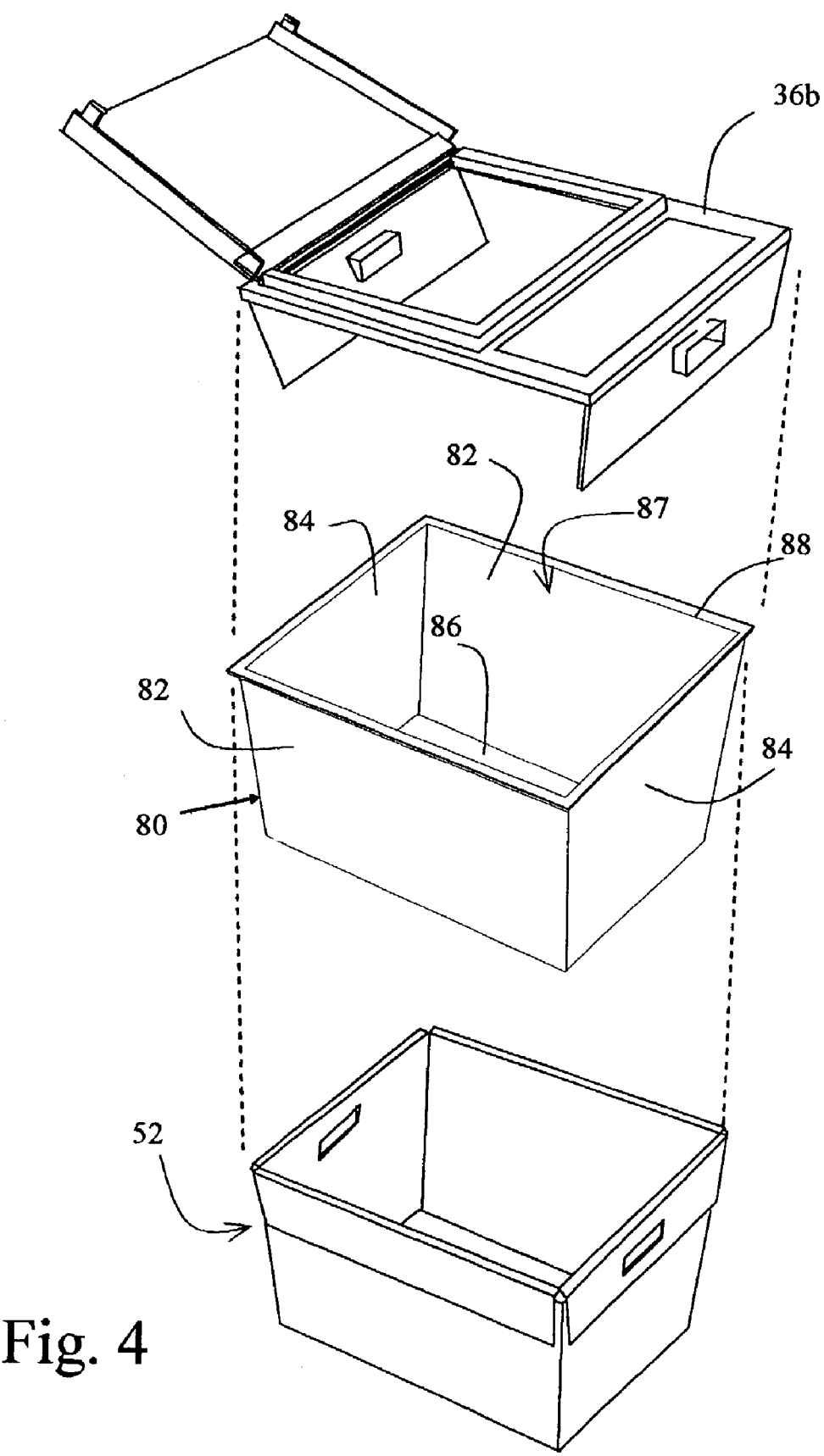
FIG. 4 is an exploded perspective view of a mail tub liner which may be used in conjunction with the embodiment of FIG. 3.

FIG. 4 shows a one-piece, non-permeable rectangular liner 80 which may be used in conjunction with the mail receptacle 50 and included between standard mail flats tub 52 and top cover 36a as shown in the exploded view. Liner 80 is constructed from a vacuum formed plastic, such as low density polyethylene, to have two opposing sides 82 and two opposing ends 84, which are all canted inwardly towards a bottom 86 so that liner 80 fits completely within standard mail flats tub 52. Liner 80 includes an open top 87 surrounded by a peripheral top edge 88. Top edge 88 is designed to be pinched between top cover 36b and standard tub 52 to thereby substantially seal liner 80 against top cover 36b. Liner 80 is thus designed to retrofit with standard mail flats tub 52.

In this manner, rectangular tub 52 is a standard mail flat tub with the mail receptacle further including a non-permeable liner 80 located within the common mail flat tub. The liner may include an open top 87, and top cover 36a may include a peripheral frame 66 (FIG. 3) adapted to engage open top 53 (FIG. 3) of rectangular tub 52 and open top 87 of liner 80.

Figure 5:
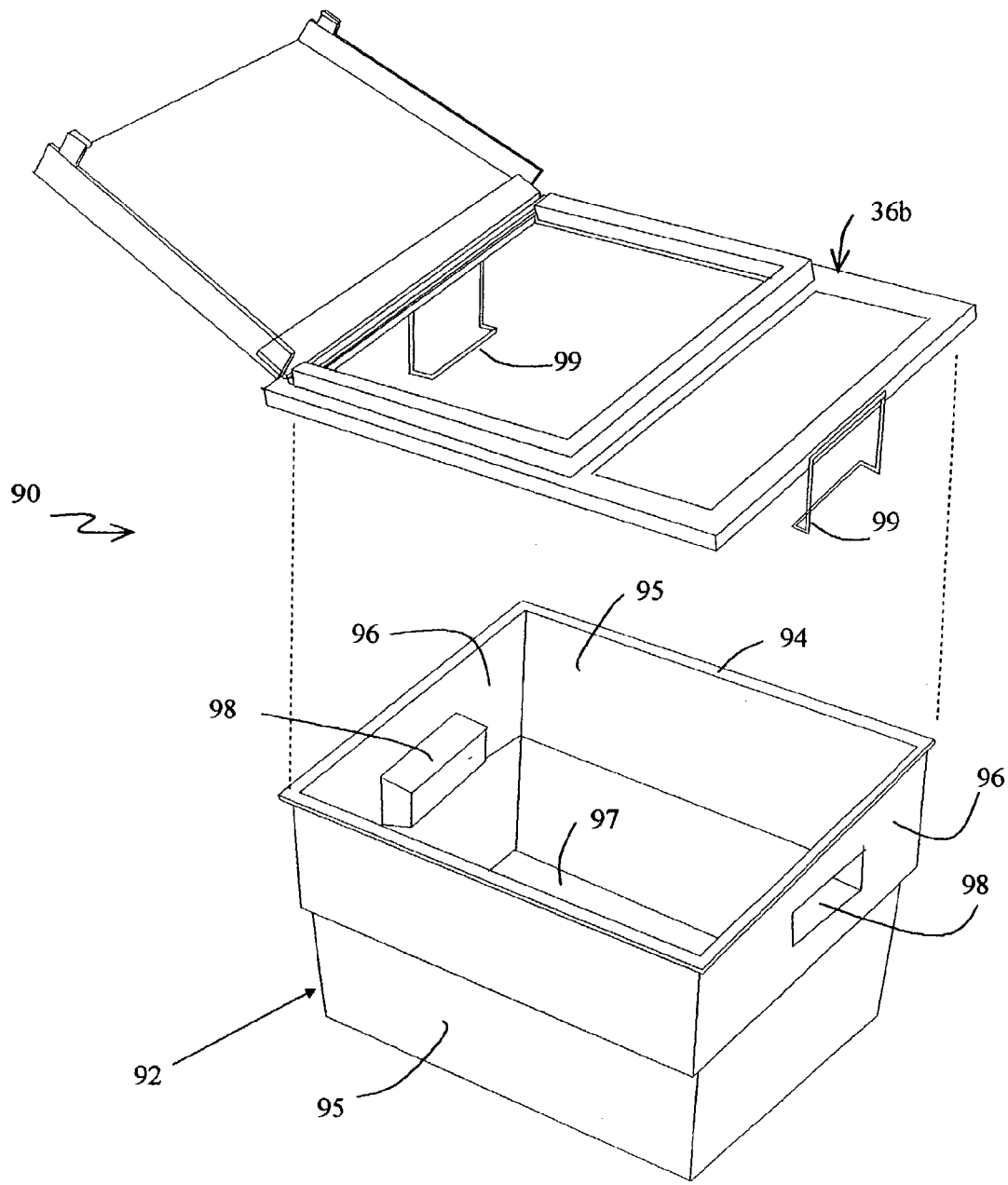
FIG. 5 is an exploded perspective view of a mail receptacle constructed in accordance with yet another embodiment of the present invention.

FIG. 5 shows an exploded view of a mail receptacle 90 constructed in accordance with another embodiment of the present invention and intended as a complete replacement for a standard mail flats tub 16 (FIG. 1). Mail receptacle 90 generally includes a non-permeable rectangular tub 92 and top cover 36b. Rectangular tub 92 is constructed from a vacuum formed plastic, such as ABS plastic, and includes two opposing sides 95, two opposing ends 96 and a bottom 97. Ends 96 each includes a hand grip 98 to facilitate handling of tub 92. Sides 95, ends 96 and hand grips 98 may be canted in a manner to allow at least limited nesting of multiple tubs 92. Tub 92 includes a peripheral edge 94 which may be sized to match top edge 59 (FIG. 3) to match that of standard mail flats tub 52 (FIG. 3) and thereby be interchangeable with other embodiments of the present invention.

Top cover 36b is identical to top cover 36a (FIG. 3), except for the absence of end extensions 72 (FIG. 3). Due to the lack of through hand holes in tub 92, extensions 72 are not necessary to seal such hand holes. However, it is still helpful to have top cover 36b engage tub 92, so cover 36b includes a separate latch 99 affixed to each end of frame 66 and adapted to engage respective hand grips 98. Alternatively, top cover 36a (FIG. 3) may be used with tub 92. Likewise, top cover 36b may alternatively be used with tub 52 and liner 80 of FIG. 4.

In this manner, rectangular tub 92 includes a separate manual grip 98 located on two opposing ends of rectangular tub 92, and top cover 36b may be adapted to engage manual grips 98 to maintain engagement between peripheral frame 66 and open top 95.

Figure 6:
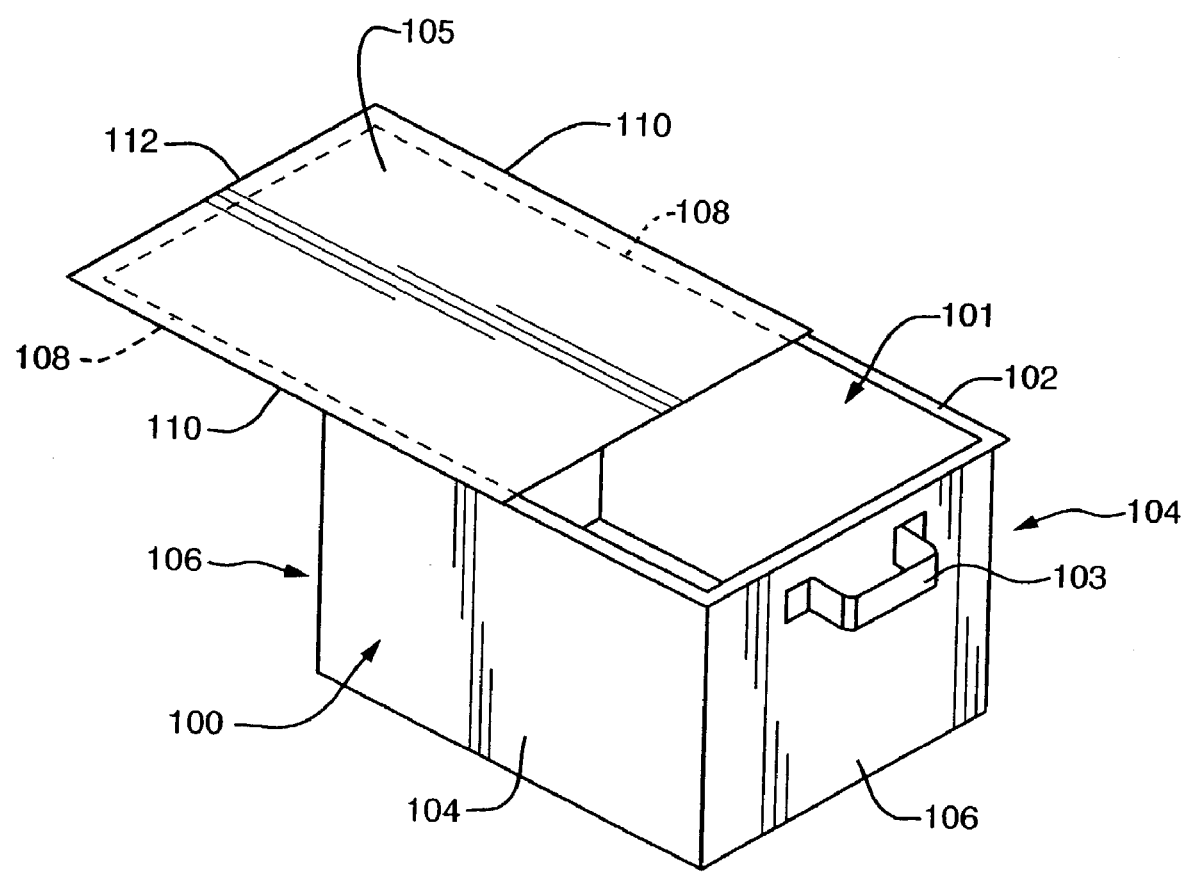
FIG. 6 is a perspective view of a mail receptacle constructed in accordance with still another embodiment of the present invention.

FIG. 6 is a perspective view of a mail receptacle 100 constructed in accordance with yet another embodiment of the present invention. Mail receptacle 100 is rectangular and includes an open top 101, two opposing sides 104, two opposing ends 106, and a closed bottom. Also included is a horizontal, outwardly extending flange 102 formed around open top 101. Ends 106 each includes a handle 103 affixed to the outside thereof. Cover 105 is rectangular and includes a peripheral lip 108 located along opposing sides 110 and one end 112. Cover 105 and lip 108 are adapted to engage the horizontal flange 102 of receptacle 100. The circumferential arrangement of flange 102 allows cover 105 to be engaged therewith from either end 106 of receptacle 100. Likewise lip 108 may be constructed just on opposing sides 110 and not along end 112 of cover 105 to enable the engagement of cover 105 from either end thereof. Seals (not shown) may be located along opposing ends of cover 105 to further isolate the contents of mail receptacle 100. Alternatively, suitable seals may be located along the top edge of opposing ends 106. Mail receptacle 100 may be formed from any suitable, durable, non-permeable material, such as plastic or aluminum.

Figure 7:
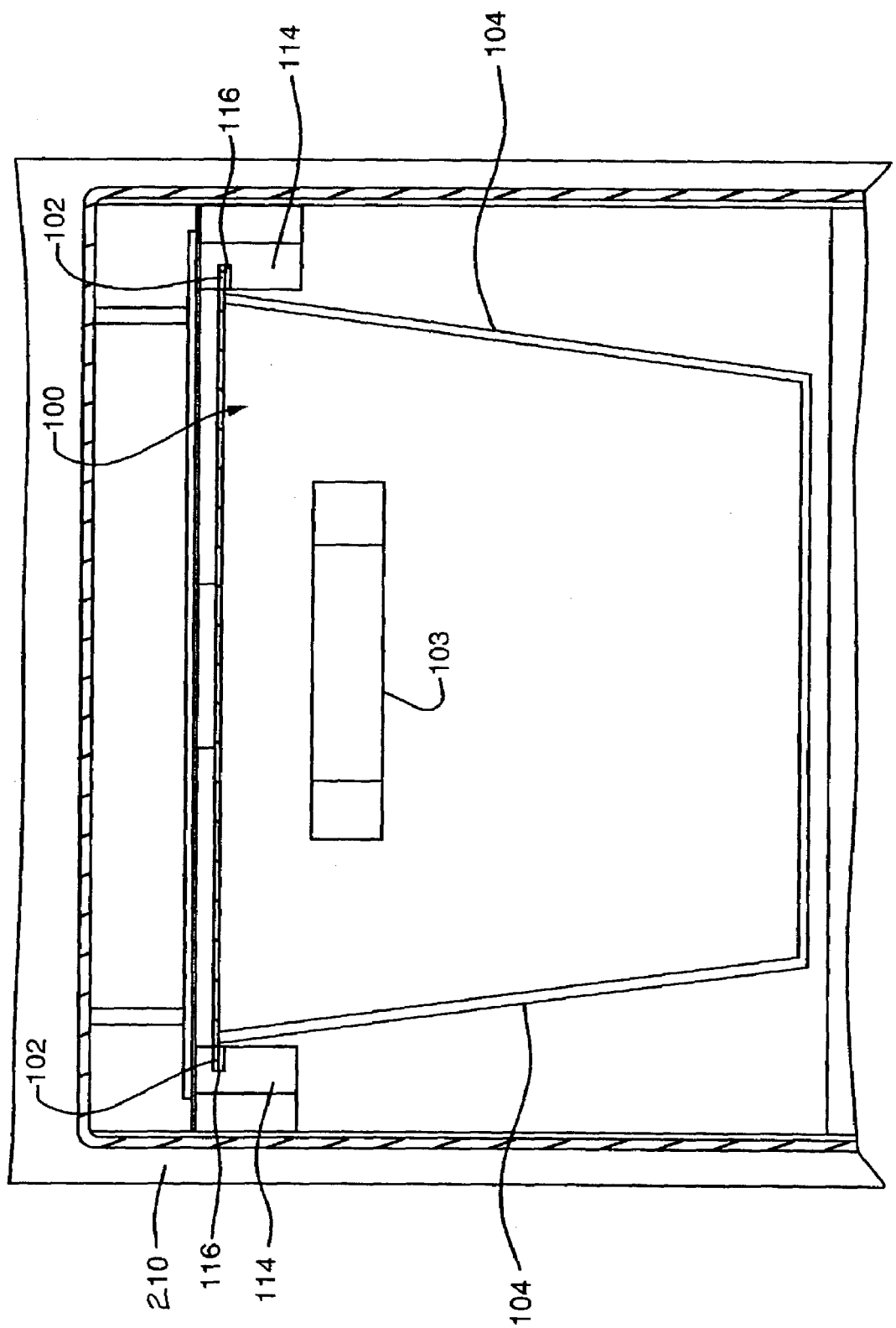
FIG. 7 is a partial diagram of a mail box within which is located the mail receptacle of FIG. 6.
Figure 8:
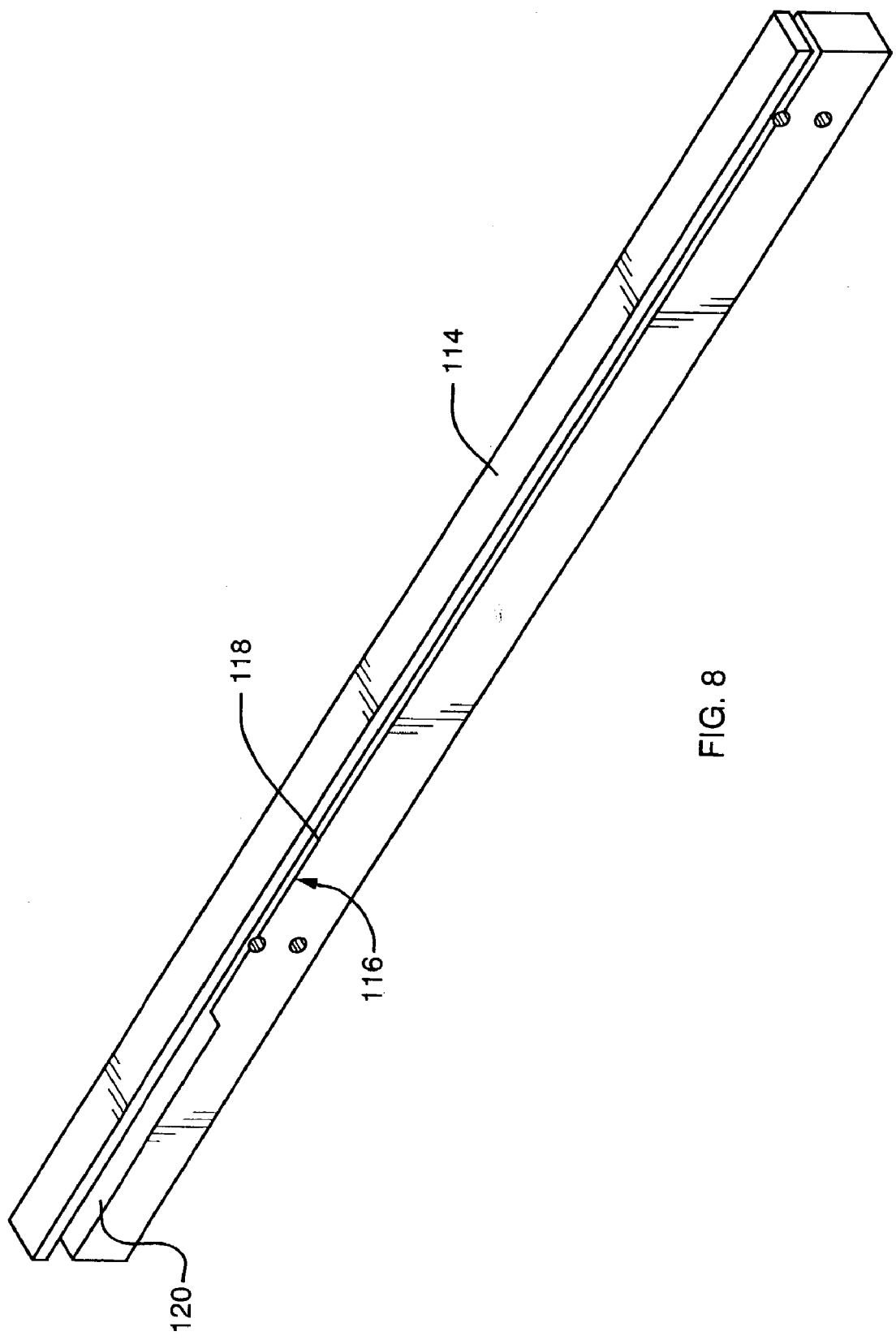
FIG. 8 is a perspective view of a portion of the mail box of FIG. 7.

FIG. 7 shows a side view of a portion of a mail box 210, which portion includes the closeable container 100 without a cover. Flange 102 is engaged by a pair of guide rails 114. Guide rails 114 are affixed to mail box 210 to engage the flange 102 on opposing sides 104 of container 100 and to support container 100. Guide rails 114 each include a slot 116 for accepting flange 102 (FIG. 6). A guide rail 114 is shown in greater detail in FIG. 8, with slot 116 including a narrower portion 118 and a wider portion 120.

In this manner, rectangular tub 100 includes a peripheral flange 102 extending horizontally outwardly from around open top 101, and top cover 105 is adapted to engage flange 102 for closing tub 100. Top cover 105 is adapted to engage flange 102 and close tub 100 during removal of tub 100 from a drop box 210. Top cover 105 may be rectangular and include a lip 108 on at least two opposing sides 110, which lip 108 is adapted to engage flange 102.

Figure 9:
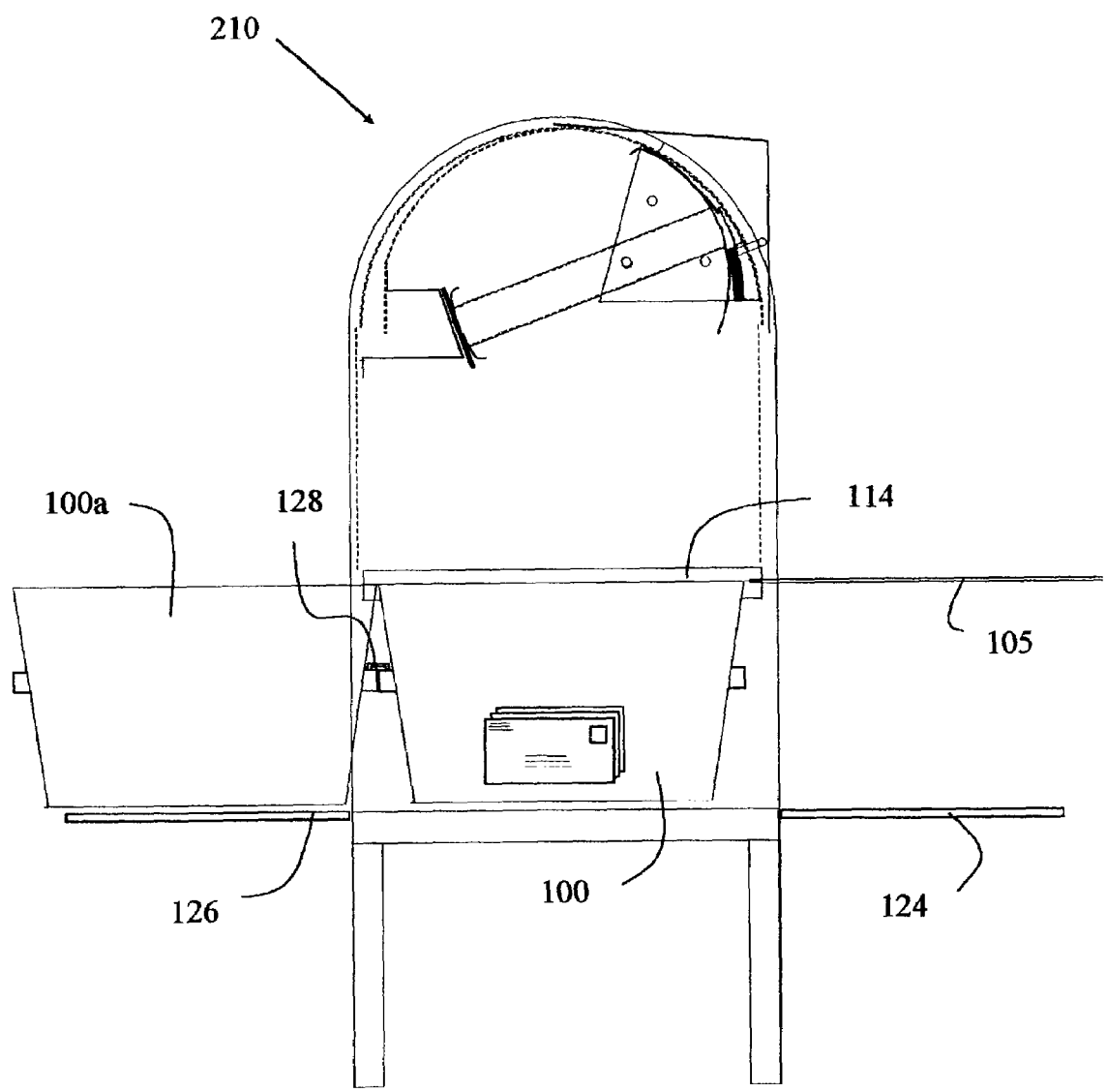
FIG. 9 is a side view diagram of a mail box constructed in accordance with the mail box of FIGS. 6–8.

FIG. 9 shows the application of mail receptacle 100 to a mail box 120, which shows one of a pair of horizontal, opposed rails 114 designed to support mail receptacle 100 by flange 102 along opposing sides 104. Cover 105 may be engaged with flange 102 and mail receptacle 100 as receptacle 100 is pulled from mail box 210 thus limiting the exposure of a mail carrier to the contents of mail receptacle 100. Mail receptacle 100 may be both installed and removed through a single securable door 124 in mail box 210, or a second, empty mail receptacle 100a may be installed through a second securable door 126 as mail receptacle 100 is removed.

Handles 103 of mail receptacles 100, 100a may be identically constructed to abut each other as shown, or a coupler 128 may be used to attach mail receptacles 100, 100a. Thus one tub 100 is removed while another tub 100a is inserted, and the process may include pushing or pulling.

In this manner, flange 102 is adapted to engage separate opposing rails 114 within drop box 210 for substantially supporting tub 100. Top cover 105 is adapted to engage opposing rails 114 and to thereby engage flange 102 with removal of tub 100 from the drop box 210. A first tub 100a is adapted to abut a second tub 100 as first tub 100a is being inserted into drop box 210 and thereby push second tub 100 from drop box 210 in the process of the first tub 100a being pushed into drop box 210. Alternatively, a first tub is adapted to be coupled to a second tub as the first tub is being removed from drop box 210 and thereby pull second tub into drop box 210 in the process of the first tub being pulled from drop box 210.

The present invention is illustratively described above in reference to the disclosed embodiments. Various modifications and changes may be made to the disclosed embodiments by persons skilled in the art without departing from the scope of the present invention as defined in the appended claims.

What is claimed is:

1. A closeable mail receptacle for use inside of a mail drop box having a depository port and a door, comprising:
   a rectangular tub for positioning inside said drop box, said tub including two opposing sides, two opposing ends and a bottom whereby said tub defines an open top for receiving mail articles; and
   a top cover for positioning inside said drop box and for opening and closing said tub while said tub is positioned inside said drop box, said top cover engaging said open top and closing said tub either prior to or during removal of said tub from said drop box.

2. The closeable mail receptacle of claim 1, wherein said rectangular tub includes a peripheral edge surrounding said open top, and further wherein said top cover includes a peripheral frame adapted to engage said peripheral edge.

3. The closeable mail receptacle of claim 2, wherein said top cover is further adapted to engage said rectangular tub to maintain engagement between said peripheral frame and said peripheral edge.

4. The closeable mail receptacle of claim 2, wherein said top cover includes an opening for receiving mail articles and a door adapted for closing said opening prior to removal of said receptacle from said drop box.

5. The closeable mail receptacle of claim 4, wherein said door is hinged to said peripheral frame.

6. The closeable mail receptacle of claim 4, wherein said frame or said door is a single molded piece of polyethylene terephthalte glycol.

7. The closeable mail receptacle of claim 4, wherein said door is hinged to said frame by a living hinge.

8. The closeable mail receptacle of claim 7, wherein said living hinge is molded from polyvinyl chloride and is affixed to said door and said frame.

9. The closeable mail receptacle of claim 1, wherein
said top cover includes a separate end extension located at two opposing ends of said top cover and arranged to squeeze the opposing sides of said rectangular tub.

10. The closeable mail receptacle of claim 9, wherein said rectangular tub is a mail flat tub having a separate hand hole located on the opposing ends of said rectangular tub, and further wherein said end extensions are adapted to close said hand holes when said top cover engages said rectangular tub.

11. The closeable mail receptacle of claim 10, wherein said end extensions include hand cups adapted for location within said hand holes in said mail flat tub and adapted to allow manual insertion to facilitate handling of said mail flat tub with said top cover.

12. A closeable mail receptacle for use inside of a mail drop box having a depository port and a door, comprising:
rectangular tub for positioning inside said drop box, said tub having an open top; and
a top cover for positioning inside said drop box and for opening and closing said tub while said tub is positioned inside said drop box, said top cover engaging said open top and closing said tub either prior to or during removal of said tub from said drop box;
said rectangular tub being a mail flat tub and further comprising a non-permeable liner located within said mail flat tub.

13. The closeable mail receptacle of claim 12, wherein said liner includes an open top, and said top cover further comprising a peripheral frame adapted to engage said open top of the rectangular tub and said open top of said liner.

* * * * *